(12) United States Patent
Syvret et al.

(10) Patent No.: US 7,771,611 B2
(45) Date of Patent: Aug. 10, 2010

(54) OXYPENTAFLUOROSULFATE COMPOSITIONS AND PROCESSES FOR MAKING THEM

(75) Inventors: Robert George Syvret, Allentown, PA (US); Gauri Sankar Lal, Whitehall, PA (US); Kristen Elaine Minnich, Germansville, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 1065 days.

(21) Appl. No.: 11/484,374

(22) Filed: Jul. 10, 2006

(65) Prior Publication Data
US 2008/0033164 A1 Feb. 7, 2008

(51) Int. Cl.
| | |
|---|---|
| C09K 3/00 | (2006.01) |
| C01B 21/22 | (2006.01) |
| C01B 21/24 | (2006.01) |
| C01B 21/086 | (2006.01) |
| C01B 9/08 | (2006.01) |
| C01B 17/45 | (2006.01) |
| C07F 9/02 | (2006.01) |
| C07C 279/04 | (2006.01) |
| C07C 211/63 | (2006.01) |
| C07C 211/62 | (2006.01) |
| C07D 295/04 | (2006.01) |
| C07D 207/323 | (2006.01) |
| C07C 211/64 | (2006.01) |

(52) U.S. Cl. .............................. 252/182.11; 252/182.17; 252/182.32; 252/182.33; 423/386; 423/400; 423/405; 423/464; 423/467; 546/184; 546/347; 548/579; 564/12; 564/101; 564/240; 564/281; 564/282; 564/291; 564/295

(58) Field of Classification Search ............ 252/182.11, 252/182.17, 182.32, 182.33; 423/386, 400, 423/405, 464, 467; 546/184, 347; 548/579; 564/12, 101, 240, 281, 282, 291, 295
See application file for complete search history.

(56) References Cited

U.S. PATENT DOCUMENTS 3,769,312 A 10/1973 Gould et al

FOREIGN PATENT DOCUMENTS

DE 19 28 539 A1 12/1969

OTHER PUBLICATIONS

Schack, C., et al; "Vibrational Spectrum and Force Constants of the SF50- Anion"; Inorganic Chemistry; vol. 12, No. 3; 1973; pp. 620-622; XP002455438.
Heilermann, et al; "Hexakoordinierte Schwefel (VI) und -Hexakoordinerte Schwefel (IV)-Anionen"; Chemische Berichte; vol. 122; pp. 427-432; XP009091107.
Schack, C.J., et al; "Synthesis of SF0- Substituted Fluorocarbons"; Journal of Fluorine Chemistry; Elsevier, Amsterdam, NL; vol. 45, No. 2; Nov. 1, 1989; pp. 283-291; XP000047370.
Lustig, R.; "Studies Involving Some Nonmetal Oxy- and Thiofluoride Salts"; Inorganic Chemistry; vol. 6, No. 11; 1967; pp. 2115-2117; XP002455437.
Place, Willisamson; "The Preparation and Characterization of Some New Pentafluorosulfuroxyalkanes and— Alkenes"; Journal of the American Chemical Society; 1968; vol. 90; pp. 2550-2556; XP002463747.
Schack, Christie; Introduction of Functional Groups into Some Chlorofluorocarbon Ethers; Journal of Fluorine Chemistry; 1979; vol. 14; pp. 519-522; XP002463748.
Marcellis, Eibeck; "Synthesis of Pentafluorosulfuroxydifluoroacetyl Fluoride"; Journal of Fluorine Chemistry; 1975; vol. 5; pp. 71-75; XP002463749.
Lowell Ray Anderson, et al; "Perhaloalkyl Hypochlorites and Pentafluorosulfur Hypochlorite. IV. Reactions with Olefins"; Journal of Organic Chemistry, American Chemical Society, Easton, US; 1970; vol. 35, No. 11; pp. 3730-3733; XP009090914.
Krum, Kirchmeier, Shreeve; "Synthesis, Isolation and Chemistry of Perfluorinated Difluorocarbimides: Precursors to New Perfluorinated Tetrazanes"; Inorganic Chemistry; 1995; vol. 34; pp. 5049-5054; XP002463750.
Vij, Kirchmeier, et al; "Perfluorovinylamines: Reactions of the Perfluorovinyl Group with Nucleophiles and Electrophiles"; Inorganic Chemistry; 1993; vol. 32; pp. 5011-5020; XP002463751.
Case, J.R., et al; "Pentafluorosulphuroxy-Derivatives of Hexafluoropropene"; Journal of the Chemical Society, Chemical Society; Letchworth, GB; 1964; pp. 946-948; XP009090925.
Williamson, et al; "On the Reaction of Pentafluorosulfur Hypofluorite with Unsymmetrical Two-Carbon Alkenes"; Inorganic Chemistry, American Chemical Society; Easton, US; Apr. 1963; vol. 2, No. 2; pp. 421-422' XP009090938.
Williamson, et al; "Reactions of Pentafluorosulfur Hypofluorite"; Inorganic Chemistry, American Chemical Society; Easton, US; Aug. 1962; vol. 1, No. 3; pp. 673-677; XP009090939.

(Continued)

Primary Examiner—Peter G O'Sullivan
(74) Attorney, Agent, or Firm—Lina Yang

(57) ABSTRACT

Novel compositions are provided containing a compound represented by the formula $YOSF_5$ or $ZOSF_5$, where: (a) Y is: (i) an organic cation other than $(Me_2N)_3S^+$ or (ii) an inorganic cation, provided that when Y is the inorganic cation, the composition further includes a complexing agent; and (b) Z is $C_{1-20}$ alkyl, aryl, cycloalkyl, combinations thereof, or analogues thereof containing at least one heteroatom, provided that the compound represented by the formula $ZOSF_5$ is a molecular compound. Processes of making the cationic compounds are disclosed as are processes for using the compositions containing cationic compounds in nucleophilic replacement reactions to prepare the compositions containing molecular compounds including the $OSF_5$ group.

13 Claims, No Drawings

OTHER PUBLICATIONS

Duncan, et al; "The Preparation and Properties of Trifluoromethoxy Sulfur Pentafluoride [CF3OSF5] and cis-bis (trifluoromethoxy)tetrafluorosulfur (VI) [CF3O)2SF4]"; Inorganic Chemistry, American Chemical Society; Easton, US; 1964; vol. 3, No. 6; pp. 850-852; XP009090936.

Max Lustig, et al, "Studies Involving Some Nonmetal Oxy- and Thiofluoride Salts," Inorg. Chem., 6, 1967, pp. 2115-2117.

Karl O. Christie, et al, "Vibrational Spectrum and Force Constants of the SF5O Anion," Inorg. Chem. 12, 3, 1973, pp. 620-622.

Rudiger Mews, et al, "Hexa-coordinated Sulfur (VI) Anions," Chem. Ber. 122, 1989, pp. 427-432.

Heilermann, et al; "Hexakoordinierte Schwefel (VI) und -Hexakoordinerte Schwefel (IV)-Anionen"; Chemische Berichte; vol. 122; pp. 427-432; XP009091107.

Schack, C.J., et al; "Synthesis of SF0- Substituted Fluorocarbons"; Journal of Fluorine Chemistry; Elsevier, Amsterdam, NL; vol. 45, No. 2; Nov. 1, 1989; pp. 283-291; XP000047370.

OXYPENTAFLUOROSULFATE COMPOSITIONS AND PROCESSES FOR MAKING THEM

BACKGROUND OF THE INVENTION

The present invention pertains to novel oxypentafluorosulfate compositions, and processes for making such compositions.

The literature currently identifies two compounds containing the $OSF_5$ anion. The first compound, $CsOSF_5$, is disclosed in, e.g., Lustig et al., "Studies Involving Some Nonmetal Oxy- and Thiofluoride Salts." Inorg. Chem., 6, 2115 (1967), and Christe et al., "Vibrational Spectrum and Force Constants of the $SF_5O^-$ Anion." Inorg. Chem., 12, 620 (1973). $CsOSF_5$ is an inorganic salt, which has little or no solubility in common organic solvents. As a result of its insolubility, the compound itself has no utility as a source of $OSF_5$ anions in substitution reactions. The second compound is $(Me_2N)_3S^{+-}OSF_5$, as disclosed in, e.g., Mews et. al., "Hexa-coordinated sulfur (VI) anions." Chem. Ber. 122 (1989) 427-432. The second compound, although soluble in common organic solvents, has not been demonstrated as an effective source of nucleophilic $OSF_5$.

Accordingly, it is desired to provide novel compositions comprising oxypentafluorosulfate anions, which are sufficiently soluble in common organic solvents so as to be suitable for use in nucleophilic displacement reactions. It is further desired to provide novel products produced by such reactions.

All references cited herein are incorporated herein by reference in their entireties.

BRIEF SUMMARY OF THE INVENTION

Accordingly, a first aspect of the invention comprises a composition comprising a compound represented by the formula $YOSF_5$ or $ZOSF_5$, where:

(a) Y is: (i) an organic cation other than $(Me_2N)_3S^+$ or (ii) an inorganic cation, provided that when Y is the inorganic cation, the composition further comprises a complexing agent; and (b) Z is a member selected from the group consisting of $C_{1-20}$ alkyl, aryl, cycloalkyl, combinations thereof, and analogues thereof containing at least one heteroatom and/or halogen, provided that the compound represented by the formula $ZOSF_5$ is a molecular compound.

A second aspect of the invention comprises a composition represented by the formula $YOSF_5$, where Y is an organic cation other than $(Me_2N)_3S^+$.

A third aspect of the invention comprises a composition represented by the formula $ZOSF_5$, where Z is $C_{1-20}$ alkyl, aryl, cycloalkyl, combinations thereof, and analogues thereof containing at least one heteroatom and/or halogen, wherein the composition is a molecular compound.

A fourth aspect of the invention comprises a composition comprising: (a) a compound represented by the formula $YOSF_5$, where Y is an inorganic cation; and (b) a complexing agent.

A fifth aspect of the invention comprises a process for providing the composition of the third aspect of the invention, said process comprising:

providing a reagent represented by the formula $Y^{+-}OSF_5$, where Y is an organic cation;

providing a substrate represented by the formula ZL, where L is a leaving group;

combining the reagent and the substrate in a solvent; and substituting $OSF_5$ for the leaving group so as to provide $ZOSF_5$.

A sixth aspect of the invention comprises a process for providing the composition of the third aspect of the invention, said process comprising:

providing a reagent represented by the formula $Y^{+-}OSF_5$, where Y is an inorganic cation;

providing a complexing agent;

providing a substrate represented by the formula ZL, where L is a leaving group;

combining the reagent, the complexing agent and the substrate in a solvent; and substituting $OSF_5$ for the leaving group so as to provide $ZOSF_5$.

A seventh aspect of the invention comprises a process for providing the composition of the first aspect of the invention, wherein Y is the organic cation, said process comprising:

providing a reagent represented by the formula YF; and reacting the reagent with $SOF_4$ in a solvent so as to provide $YOSF_5$.

An eighth aspect of the invention comprises a process for providing the composition of the first aspect of the invention, wherein Y is the inorganic cation and the composition further comprises a complexing agent, said process comprising:

providing a reagent represented by the formula YF; and reacting the reagent with $SOF_4$ in a solvent so as to provide $YOSF_5$, wherein the complexing agent is combined with the reagent before reacting the reagent with $SOF_4$, and/or is combined with the $YOSF_5$.

DETAILED DESCRIPTION OF THE INVENTION

The invention provides novel compositions containing $OSF_5$, and processes for making such compositions.

In embodiments of the invention in which the composition comprises an $OSF_5$ anion, the anion finds utility as a nucleophilic source of $OSF_5$, and as such, can be used as a nucleophile to add the $OSF_5$ functional group to desired substrates by way of a nucleophilic displacement reaction. The resulting novel compounds constitute another embodiment of the invention. It is believed that one or more of the following properties will be modified in the inventive compound relative to its unsubstituted analog: (a) electronegativity; (b) lipophilicity; (c) oxidation resistance; (d) thermal stability; (e) chemical stability; (f) steric bulk; (g) selectivity in chemical transformations; and (h) dielectric properties.

Thus, the process of substituting $OSF_5$ on a compound is also useful as a means for modifying the properties of the compound. For example, $OSF_5$ substitution will be a useful alternative to $CF_3$ substitution with fewer environmental concerns, since $OSF_5$ may be biodegradable. Polymers can be modified with $OSF_5$ to provide the resulting products with improved properties such as chemical resistance, stain resistance, etc.

Organic Cation Embodiments

The organic cation embodiments of the invention are compositions of the invention represented by the formula $Y^{+-}OSF_5$ (or simply $YOSF_5$), where Y is an organic cation. The organic cation is sufficiently soluble in solvents, such that the $OSF_5$ anion is suitable for use as a nucleophile in nucleophilic displacement reactions.

The organic cation embodiments are preferably soluble in solvents, including but not limited to, acetone, halogenated hydrocarbons such as dichloromethane (DCM) and chloroform, dimethylformamide (DMF), dimethylsulfoxide (DMSO), ethers such as tetrahydrofuran (THF) and diethylether (DEE), nitriles such as acetonitrile (ACN), hydrocarbons, hexanes, and aromatic hydrocarbons, such as toluene. A composition is defined herein as soluble in a solvent if at least 1 mg will dissolve in a liter of the solvent.

Suitable organic cations include without limitation compounds containing quaternary nitrogen atoms (nitrogen atoms with four bonds), such as compounds represented by the following formula:

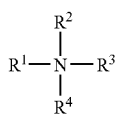

where each of $R^1$, $R^2$, $R^3$ and $R^4$ is independently selected from the group consisting of $C_{1-20}$ alkyl, aryl, and combinations thereof, as well as analogues containing heteroatoms such as O, S, Si, P, and N. Preferably, the organic cation is a member selected from the group consisting of $C_{1-20}$ tetraalkyl- and tetraarylammonium and combinations thereof, hexamethylguanidinium, methylhexamethylenetetramine (Structure 1 below), N,N,N-trimethyl-1-adamantylammonium (Structure 2), N-methylquinuclidinium (Structure 3), N,N'-dimethyltriethylenediammonium (Structure 4), 1,1,3,3,5,5-hexamethylpiperidinium (Structure 5), phosphazenium (Structure 6), imidazolium (Structure 7), pyridinium (Structure 8), and tris(dimethylamino)sulfonium (TAS) (Structure 9). However, in certain embodiments of the inventive composition, the organic cation is not TAS.

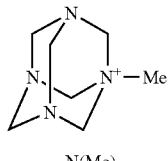

1

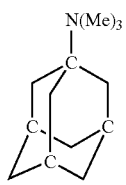

2

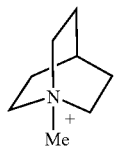

3

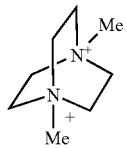

4

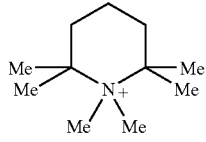

5

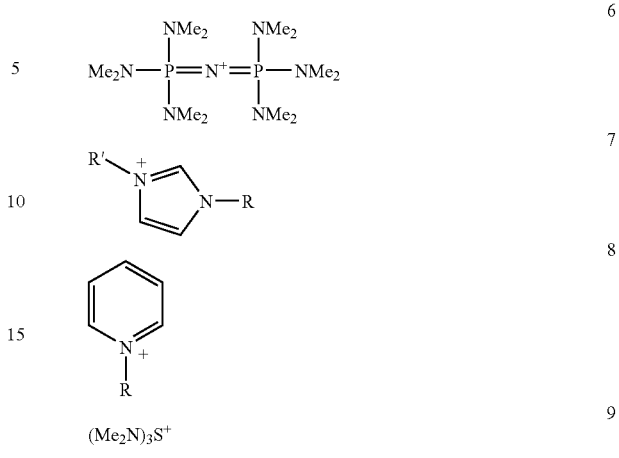

Process for Making Organic Cation Compositions

The preferred process for making the organic cation compounds comprises providing a reagent represented by the formula YF, and reacting the reagent with $SOF_4$ in a solvent so as to provide $YOSF_5$.

Preferred solvents for this process include any aprotic solvent, including but not limited to, ACN, DCM, DMF, and $SO_2ClF$.

Inorganic Cation Embodiments

The inorganic cation embodiments of the invention are compositions of the invention comprising a complexing agent and a compound represented by the formula $Y^{+-}OSF_5$ (or simply $YOSF_5$), where Y is an inorganic cation.

The complexing agent should render the composition (particularly the inorganic cation) sufficiently soluble in solvents, such that the $OSF_5$ anion is suitable for use as a nucleophile in nucleophilic displacement reactions. Suitable complexing agents include without limitation 18-crown-6 and derivatives thereof such as 1,10-diaza-18-crown-6, cryptands, fluorocryptands, polyethers, crown ethers, fluorocrown ethers, crown thioethers, calixarenes such as dihydrocalix[4]arene crown-6 ether, polyamines and polyamides, and porphyrins. In certain embodiments, the amount of complexing agent sufficient to render the composition soluble is typically 0.5 to 2 complexing agents per inorganic cation, although exceptions are possible.

Suitable inorganic cations include but are not limited to Cs, Rb, K, Na, Li, NO and $NO_2$, with Cs being preferred. However, certain inorganic cation (as well as certain organic cation) embodiments of the invention are free of Cs.

Process for Making Inorganic Cation Compositions

The preferred process for making the inorganic cation compositions comprises: (a) providing a reagent represented by the formula YF; and (b) reacting the reagent with $SOF_4$ in a solvent so as to provide $YOSF_5$, wherein the complexing agent is combined with the reagent before reacting the reagent with $SOF_4$, and/or is combined with the $YOSF_5$.

Preferred solvents for this process include any aprotic solvent, including but not limited to, ACN, DCM, DMF, and $SO_2ClF$.

Nucleophilic Displacement Process

In another aspect of the invention, there is provided a process for displacing a leaving group, L, from a substrate, Z, with the $OSF_5$ anion. The process is represented by the following equation:

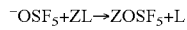

$$^{-}OSF_5 + ZL \rightarrow ZOSF_5 + L$$

The substrate, Z, is preferably $C_{1-20}$ alkyl, aryl, cycloalkyl, and combinations thereof, wherein each may be substituted by alkyl, aryl, cycloalkyl, halogen, and heteroatom groups such as O, N, S, Si, and P.

The leaving group, L, is preferably halide, haloalkyl, triflate, tosylate, mesylate, nosylate, teflate, diazonium salts, sulfonate, sulfonium, and alkyl- and perfluoroalkyl sulfonamides.

The nucleophilic displacement process is initiated by combining the reagent (i.e., the source of the $OSF_5$ anion) and the substrate in a solvent. The reagent is a composition in accordance with the invention, as described above. Accordingly, suitable solvents include without limitation those solvents mentioned above with respect to the solubility of the compositions of the invention.

Products of the Displacement Process

The displacement process preferably provides novel compounds containing $OSF_5$. In preferred embodiments, the compounds are represented by the formula $ZOSF_5$, where Z is preferably $C_{1-20}$ alkyl, aryl, cycloalkyl, and combinations thereof, and wherein each may be substituted by alkyl, aryl, cycloalkyl, halogen, and heteroatom groups such as O, N, S, Si, and P. In other preferred embodiments, the composition is represented by the formula $R^1R^2C(X)C(OSF_5)R^3R^4$, where X is halogen, and each of $R^1$, $R^2$, $R^3$ and $R^4$ is independently hydrogen, $C_{1-18}$ alkyl, aryl, and combinations thereof, as well as analogues containing heteroatoms such as O, S, Si, P, and N.

EXAMPLES

The invention will be illustrated in more detail with reference to the following Examples, but it should be understood that the present invention is not deemed to be limited thereto.

Example 1

Preparation of Tetramethylammonium oxypentafluorosulfate, $(CH_3)_4N^{+-}OSF_5$

In the dry atmosphere of a $N_2$ glovebox, a 300-cc stirred reactor (Parr Instrument Co.) was loaded with 5.35 g (57.4 mmol) of white crystalline tetramethylammonium fluoride and 110 mL of anhydrous $CH_3CN$. The reactor was sealed under $N_2$ and brought out of the glovebox. The reactor was connected to a metal vacuum system and then cooled by immersion of the reactor bottom in a Dewar of liquid $N_2$. The reactor was briefly evacuated and then 7.5 g (60.5 mmol) of pure thionyl tetrafluoride, $SOF_4$, were added. The reactor was then sealed and allowed to warm to ambient temperature. When the reactor internal temperature was 17° C., external heat was applied while the reaction mixture was stirred. The reactor contents were heated to about 75° C. over a three-hour period. The heat was shut off and the contents allowed to cool to ambient temperature overnight with stirring. The next morning the solvent and volatiles were removed by vacuum distillation. The reactor was opened in a drybox, revealing a powdery lightly brown solid.

Analysis of this solid dissolved in $CD_3CN$ by NMR confirmed the identity as $(CH_3)_4N^{+-}OSF_5$. Proton NMR results were as follows: $\delta(^1H)$=3.07 ppm, singlet (12 H on 4 methyl groups). Fluorine NMR showed an $AB_4$ pattern: $\delta(^{19}F_A)$=134.2 ppm (1F), J=159 Hz, $\delta(^{19}F_B)$=91.5 ppm (4F), J=160 Hz.

An IR spectrum of the solid (KBr pellet) showed peaks consistent with $(CH_3)_4N^{+-}OSF_5$: ν $(cm^{-1})$=1151, 785, 750, 692, 606, 530, 501.

Example 2

Preparation of Tetrabutylammonium oxypentafluorosulfate, $(Bu)_4N^{+-}OSF_5$

A sample of tetrabutylammonium fluoride, $(Bu)_4N^+F^-$, was prepared according to the method of Sun et al., JACS 127, 2050 (2005). The sample, containing approximately 19 mmol $(Bu)_4N^+F^-$ in 53 mL anhydrous $CH_3CN$, was transferred to a 300-cc stirred reactor (Parr Instrument Co) under $N_2$ and subsequently cooled to an internal temperature of about −148° C. by immersion of the reactor bottom in liquid $N_2$. The reactor was evacuated and pure $SOF_4$, 2.6 g (21.0 mmol), was condensed in. The reactor and contents were then permitted to warm to ambient temperature and stir overnight. After the specified time, $N_2$ was sparged through the reactor contents for 10 minutes and then the reactor was opened revealing a brown solution. The volatiles were removed by evaporation, leaving a residue weighing 7.3 g.

Analysis of this residue dissolved in $CDCl_3$ by NMR confirmed the identity as $(Bu)_4N^{+-}OSF_5$. Proton NMR results were as follows: $\delta(^1H)$=2.74 ppm, multiplet (8 H on 4 $CH_2$ groups), 1.19 ppm, multiplet (8 H on 4 $CH_2$ groups), 0.95 ppm, multiplet (8 H on 4 $CH_2$ groups), 0.54 ppm multiplet (12 H on 4 $CH_3$ groups). Fluorine NMR showed an $AB_4$ pattern: $\delta(^{19}F_A)$=130.5 ppm (1F), J=162 Hz, $δ(^{19}F_B)$=90.0 ppm (4F), J=160 Hz.

Example 3

Preparation of 18-crown-6 complex of $Cs^{+-}OSF_5$

In a drybox 5.28 g (19 mmol) $CsOSF_5$, 10.11 g (38 mmol) 18-crown-6, and 50 mL anhydrous acetonitrile were combined in a Schlenk flask equipped with a Teflon® coated magnetic stir bar. The flask was brought out of the drybox and the mixture stirred for about 22 hours at ambient temperature under a $N_2$ atmosphere. After the specified time the mixture was filtered and the resulting filtrate was heated under reduced pressure to remove volatiles. The resulting pale-yellow solid was analyzed by NMR spectroscopy in $CDCl_3$ and shown to be consistent with the 18-crown-6 complex of $CsOSF_5$. $^1H$ NMR: 3.32 ppm (s). Fluorine NMR showed an $AB_4$ pattern: $\delta(^{19}F_A)$=131.09 ppm (1F), J=162.8 Hz, $\delta(^{19}F_B)$=90.57 ppm (4F), J=162.6 Hz.

Example 4

Reaction of $(CH_3)_4N^{+-}OSF_5$

A slurry of tetramethylammonium oxypentafluorosulfate (0.157 g, 0.723 mmol) in acetonitrile (2 mL) was added to dodecyl trifluoromethanesulfonate (0.116 g, 0.365 mmol) in 1 mL acetonitrile and stirred for 3 hours at room temperature. Solids were removed by filtration and solvent removed by rotary evaporation. GC/MS and NMR analysis revealed a mixture of 1-fluorododecane and 1-$SF_5O$ dodecane. 1-$SF_5O$ dodecane GC/MS m/z 312, 157, 127, 111, 83, 69, 57. $^1$H NMR δ 4.5 (pent, 2H); 1.3, (20H); 0.9 (t, 3H). $^{19}$F NMR δ 79 (pent, 1F); 60 (d, 4F).

Example 5

Reaction of $(CH_3)_4N^{+-}OSF_5$

Tetramethylammonium oxypentafluorosulfate (0.129 g, 0.59 mmol), N-bromosuccinimide (0.097, 0.55 mmol) and acetonitrile (3 mL) were stirred and cooled to 5° C. A solution of cyclohexene (0.0861 g, 1.05 mmol) in acetonitrile (0.5 mL) was added to the flask. The flask contents were allowed to warm to room temperature while stirring overnight. The reaction yielded both 1-Br-2-F cyclohexane and 1-Br-2-OSF$_5$ cyclohexane. 1-Br-2-OSF$_5$ cyclohexane GC/MS m/z 225, 183, 127, 81.

Example 6

Reaction of 18-crown-6 complex of CsOSF$_5$

A solution of dodecyl trifluoromethanesulfonate (0.057 g, 0.196 mmol) in acetonitrile (0.5 mL) was added to the 18-crown-6 complex of CsOSF$_5$ (0.285 g, 0.354 mmol) dissolved in acetonitrile (2.3 mL). The reaction was stirred for 2 hours at room temperature. GC/MS analysis revealed a mixture of 1-fluorododecane and 1-SF$_5$O dodecane. 1-SF$_5$O dodecane GC/MS m/z 157, 127, 111, 97, 83, 69, 55.

While the invention has been described in detail and with reference to specific examples thereof, it will be apparent to one skilled in the art that various changes and modifications can be made therein without departing from the spirit and scope thereof.

The invention claimed is:

1. A composition comprising a compound represented by the formula YOSF$_5$, where:
   Y is: (i) an organic cation other than $(Me_2N)_3S^+$ or (ii) an inorganic cation, provided that when Y is the inorganic cation, the composition further comprises a complexing agent.

2. A composition of claim 1, where Y is an organic cation other than $(Me_2N)_3S^+$.

3. The composition of claim 2, wherein the composition is soluble in at least one solvent selected from the group consisting of acetone, halogenated hydrocarbons, dimethylformamide, dimethylsulfoxide, ethers, nitriles, hydrocarbons, hexanes and aromatic hydrocarbons.

4. The composition of claim 2, wherein the organic cation comprises a quaternary nitrogen atom.

5. The composition of claim 4, wherein the organic cation is represented by the formula

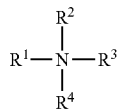

where each of $R^1$, $R^2$, $R^3$ and $R^4$ is independently selected from the group consisting of $C_{1-18}$ alkyl, aryl, combinations thereof and analogues thereof containing at least one heteroatom.

6. The composition of claim 2, wherein the organic cation is a member selected from the group consisting of $C_{1-20}$ tetraalkyl- and tetraarylammonium and combinations thereof, imidazolium, pyridinium, hexamethylguanidinium, methylhexamethylenetetramine, N,N,N-trimethyl-1-adamantylammonium, N-methylquinuclidinium, N,N'-dimethyltriethylenediammonium, 1,1,3,3,5,5-hexamethylpiperidinium, and phosphazenium.

7. A composition of claim 1,
   wherein Y is an inorganic cation; and the composition further comprises a complexing agent.

8. The composition of claim 7, wherein Y is Cs, Rb, K, Na, Li, NO, or NO$_2$.

9. The composition of claim 7, wherein the complexing agent is at least one member selected from the group consisting of 18-crown-6, 1,10-diaza-18-crown-6, cryptands, fluorocryptands, polyethers, crown ethers, fluorocrown ethers, crown thioethers, calixarenes, polyamines, polyamides and porphyrins.

10. The composition of claim 9, wherein the complexing agent is present in an amount effective to render 1 mg of the compound soluble in 1 liter of acetonitrile.

11. The composition of claim 9, wherein the amount of complexing agent is 0.5 to 2 molar equivalents of the inorganic cation.

12. A process for providing the composition of claim 1, wherein Y is the organic cation, said process comprising:
   providing a reagent represented by the formula YF; and
   reacting the reagent with SOF$_4$ in a solvent to provide YOSF$_5$.

13. A process for providing the composition of claim 1, wherein Y is the inorganic cation and the composition further comprises a complexing agent, said process comprising:
   providing a reagent represented by the formula YF; and
   reacting the reagent with SOF$_4$ in a solvent so as to provide YOSF$_5$,
   wherein the complexing agent is combined with the reagent before reacting the reagent with SOF$_4$, and/or is combined with the YOSF$_5$.

* * * * *